(12) United States Patent
Gerder et al.

(10) Patent No.: US 7,162,921 B2
(45) Date of Patent: Jan. 16, 2007

(54) MEASURING DEVICE FOR MEASURING THE VOLUME FLOW OR THE SUBSTANCE PROPERTIES OF A GAS, WHOSE DIRECTION OF FLOW CAN REVERSE

(75) Inventors: Henning Gerder, Lübeck (DE); Artur Kuo, Lübeck (DE)

(73) Assignee: Dräger Medical AG & Co. KGaA (DE)

( * ) Notice: Subject to any disclaimer, the term of this patent is extended or adjusted under 35 U.S.C. 154(b) by 77 days.

(21) Appl. No.: 11/042,785

(22) Filed: Jan. 24, 2005

(65) Prior Publication Data

US 2005/0223795 A1 Oct. 13, 2005

(30) Foreign Application Priority Data

Apr. 8, 2004 (DE) ...................... 10 2004 017 403

(51) Int. Cl.
*G01F 1/00* (2006.01)
(52) U.S. Cl. ................. 73/204.21; 73/861.52; 73/196; 73/204.11; 73/861.42; 73/861.16; 600/529; 600/538; 600/532; 128/204.22; 128/204.23; 128/203.12
(58) Field of Classification Search ............. 73/204.1; 600/529, 532, 538
See application file for complete search history.

(56) References Cited

U.S. PATENT DOCUMENTS

| | | | | |
|---|---|---|---|---|
| 2,023,568 | A * | 12/1935 | Albersheim et al. ...... | 73/861.63 |
| 4,127,121 | A * | 11/1978 | Westenskow et al. ... | 128/203.14 |
| 4,351,189 | A * | 9/1982 | Gray et al. .................. | 73/196 |
| 4,409,847 | A * | 10/1983 | Magori ..................... | 73/861.28 |
| 4,905,509 | A * | 3/1990 | Fujiwara .................... | 73/118.2 |
| 5,443,059 | A * | 8/1995 | Koch et al. ............ | 128/200.16 |
| 6,354,292 | B1 * | 3/2002 | Fisher .................... | 128/203.12 |
| 6,681,643 | B1 * | 1/2004 | Heinonen ................ | 73/861.52 |
| 2002/0116994 | A1 * | 8/2002 | Heinonen ..................... | 73/196 |
| 2003/0003029 | A1 * | 1/2003 | Rogers et al. .............. | 422/172 |
| 2005/0241387 | A1 * | 11/2005 | Miesel et al. ............ | 73/204.21 |

FOREIGN PATENT DOCUMENTS

| WO | WO 84/01704 | 5/1984 |
|---|---|---|
| WO | WO 95/06234 | 3/1995 |

\* cited by examiner

*Primary Examiner*—Edward Lefkowitz
*Assistant Examiner*—Freddie Kirkland, III
(74) *Attorney, Agent, or Firm*—McGlew & Tuttle, PC

(57) ABSTRACT

A device for measuring the volume flow or other substance properties of a gas, whose direction of flow can reverse. The arrangement contains a specially designed Y-piece, which is used for branching into direction-dependent flow paths and can be used at the same time for the measurement. Such devices can be preferably used in the area of mechanical respiration.

20 Claims, 6 Drawing Sheets

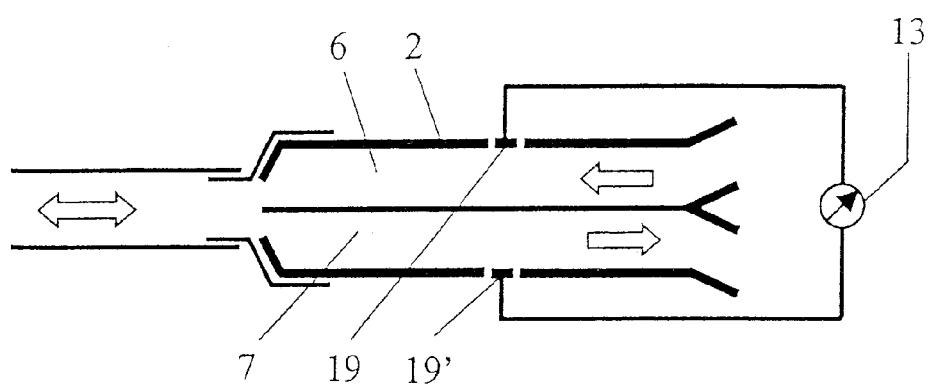
Fig. 9
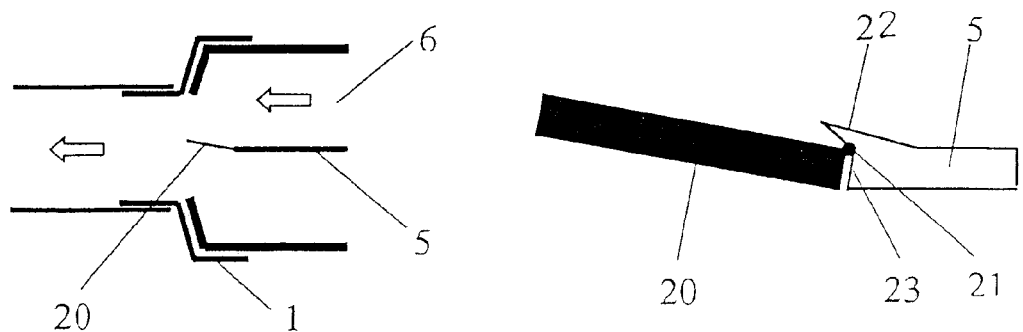
Fig. 10  Fig. 10.1

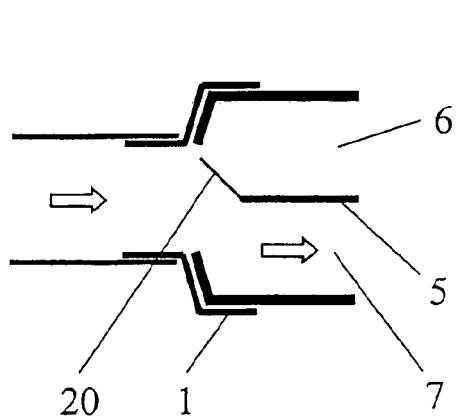
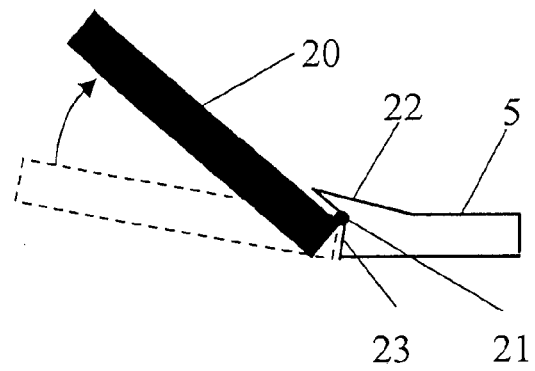
Fig. 11  Fig. 11.1
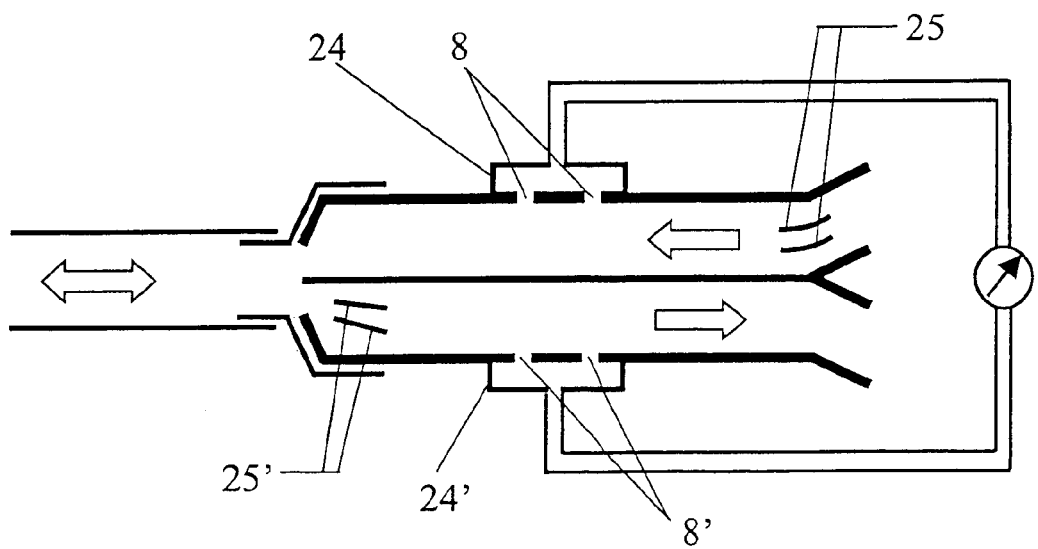
Fig. 12

US 7,162,921 B2

MEASURING DEVICE FOR MEASURING THE VOLUME FLOW OR THE SUBSTANCE PROPERTIES OF A GAS, WHOSE DIRECTION OF FLOW CAN REVERSE

CROSS REFERENCE TO RELATED APPLICATIONS

This application claims the benefit of priority under 35 U.S.C. § 119 of German Application DE 10 2004 017 403.2 filed Apr. 8, 2004, the entire contents of which are incorporated herein by reference.

FIELD OF THE INVENTION

The present invention pertains to a measuring device for measuring the volume flow or other substance properties of a flowing gas, whose direction of flow can reverse. Typical applications of such measuring devices are found in the area of artificial respiration, where the monitoring of various parameters of the breathing air is frequently a part of patient monitoring and/or contributes to the increase in the reliability of operation of the respirators. The present invention shall therefore be described based on the example of respiration technology.

BACKGROUND OF THE INVENTION

In case of mechanical respiration imitating natural respiration, the inspiration and the expiration take place via a single-channel tube introduced into the patient's trachea. Splitting into separate flow paths is performed in the vicinity of the patient via a Y-piece, and these separate flow paths can be released via actuated valves and thus make possible a desired uncoupling of the volume flows generated during expiration and inspiration, corresponding to the mode of respiration selected.

The uncoupling of the volume flows can never be complete for anatomic and technological reasons. For anatomic reasons, there is a dead volume, which is determined, among other things, by the volume of the trachea, even during natural breathing. In case of artificial respiration, the volume of the tube is a technological dead volume. If additional volume areas through which both volume flows flow are present between the outer end of the tube and the beginning of the separate flow guiding, these automatically increase the dead volume during respiration. To attain a low flow resistance during respiration, the cross section is usually expanded already in the transition area between the tube and the Y-piece. As a result, the Y-piece itself may already contribute appreciably to the technological dead volume. If additional flow-carrying components, for example, sensor heads with flow sensors, are inserted between the tube and the Y-piece, these also increase the dead volume of the respiration unit.

The dead volume may, as a rule, be tolerated if the tidal volume is markedly larger than the dead volume. However, cases in which a small tidal volume must suffice for complete respiration frequently occur during mechanical respiration in medicine. This may be due to various impairments in the functionality of the respiratory system or a small lung volume. The latter occurs mostly in neonatology. It is desirable in such cases to keep the dead volume as small as possible during artificial respiration.

It is frequently desirable to obtain the data necessary for a "real-time monitoring" of a patient possibly in the vicinity of the patient from a measurement of the gas flows being sent through the respiration unit. If flow sensors or sensors for measuring certain properties of flowing gases are directly exposed to the gas flow to be measured, they frequently yield evaluable signals only if uniform flow conditions prevail in their immediate environment and the sensors themselves do not affect the gas flow in an undefined manner. Sensors are therefore sometimes accommodated in special components which are optimized only with the aim of guaranteeing defined flow conditions in the environment of the sensor. However, the integration of additional components implies an increased effort for installation, it possibly increases the dead volume and may lead to problems in terms of optimization in the overall system if individual components are optimized concerning their individual functions but not for an optimal cooperation. One example of such an optimization concerning individual functions is the design of conventional Y-pieces. These contain an unbranched area, which can be called a base area, which is flown through in both directions and whose dimensioning is determined essentially by the conditions of connection to the tube or to a tube adapter. Furthermore, Y-pieces comprise two outflow pipes for the connection of separate flexible tubes, which are flown through in one direction only. Flexibility problems are usually the most important aspects in designing these outflow pipes. The connection sites must have a certain minimum distance for the possibility of handling and shall permit rapid mounting. As a result, difficult-to-define flow conditions may arise in the base area of the Y-pieces, where the separate flow paths are merged.

A device is known from WO 84/01704 as an example of the integration of additional components for measurement purposes, in which venturi tubes are arranged behind the Y-piece in the flow paths already extending separately, and the pressures occurring at the reduction of the area of these venturi tubes are monitored for differential pressure measurement. However, the measured values are not obtained particularly close to the patient because of the arrangement behind the Y-piece.

SUMMARY OF THE INVENTION

The object of the present invention is to provide a device for measuring the volume flow or the substance properties of a gas, whose direction of flow can reverse, which device makes it possible to obtain the measured data close to the patient and makes do with a very small dead volume, and wherein simple integration of the device into existing systems shall be possible.

A device according to the present invention for measuring the volume flow and/or additional substance properties of a gas, whose direction of flow can reverse, contains an arrangement with a Y-piece, one end of which is connected to a gas-carrying component, in which varying directions of flow may prevail, and whose other ends are connected with gas-carrying components, in which no change takes place in the direction of flow, wherein the Y-piece has separate, essentially uncoupled flow paths for gas flows of different directions of flow, which extend at least partially in parallel to one another, are separated from one another by a flat partition in the area in which they extend in parallel to one another and are equipped with means for obtaining measured values for characterizing the flowing gas in the area in which they extend in parallel to one another.

Consequently, the present invention is based, in respect to respiration technical applications, on exploring the area located in the vicinity of the tube, which is unbranched in conventional Y-pieces, as a measuring site located close to the patient, and at the same time not to allow this area to act as a dead volume any longer. The base area of the Y-piece close to the tube is divided for this purpose into two areas by a partition extending in the direction of flow. On the side facing away from the tube, each of these areas opens into the respective branch of the Y-piece, via which fresh breathing gases are supplied or the used breathing gases are removed during expiration. On the side of the Y-piece close to the tube, the partition may extend into the area of connection to the tube. The Y-piece itself does not contribute to the dead volume in this case.

Due to the flow paths being separated already in the base area of the Y-piece, it is possible to increase the overall length of the Y-piece in the base area without hereby causing an increase in the dead volume. It was found that such an increase in the overall length, in conjunction with the partition according to the present invention, causes flow conditions that permit interesting measured values to be obtained in a reliable manner from the gas flows in the area close to the patient to emerge in the areas of the Y-piece that are separated by the partition and extend in parallel.

The introduction of a partition according to the present invention reduces, in principle, the dead volume. It is especially advantageous for the flat partition to extend up to the area in which the connection with the gas-carrying component takes place, in which varying directions of flow may prevail. This area is determined mostly by a tube adapter.

An especially good uncoupling of the separate flow paths is achieved if a movable flap, which is movable between two positions, is fastened at the end of the partition, and in case of a direction of flow from the Y-piece to the gas-carrying component, in which varying directions of flow may prevail, this flap assumes a position that reduces the flow cross section as little as possible and in the reversed direction of flow it assumes a position in which it facilitates the inflow into the flow path intended for that direction of flow.

It is advantageous if at least one of the two positions of the movable flap is determined by an end stop. An especially expedient and simple embodiment of a device according to the present invention is obtained if the movable flap is fastened such that the position of the movable flap is set by the flow forces acting on the flap. The mobility of the flap can be advantageously brought about by means of elastic fastening means between the movable flap and the flat partition.

Especially favorable flow conditions, which lead to good measuring results, do arise if the cross section of the Y-piece is approximately round in the area in which the separate flow paths extend in parallel to one another. This permits, in addition, an especially simple adaptation to conventional tube adapters.

In another advantageous embodiment, the cross section of the Y-piece is approximately square in the area in which the separate flow paths extend in parallel to one another. This makes it possible to arrange chip sensors for measuring the flow in/at the outer wall of the Y-piece in an especially flow-neutral manner in the areas of the separate flow paths that extend in parallel to one another, because the planar geometry of the chips corresponds to the geometry of the flow-limiting surface.

Another advantageous embodiment is obtained if chip sensors for measuring the flow in/at the partition are arranged in the areas of the separate flow paths that extend in parallel to one another. The electric lines necessary for the operation of the chip sensors may now be integrated in the interior of the partition.

Another advantageous embodiment for flow measurement is obtained if hot wire sensors are arranged for flow measurement in the areas of the separate flow paths that extend in parallel to one another.

It may be advantageous to arrange holes, through which pressure measurement can be performed if the holes are connected with pressure measuring means via pressure pipes, in the outer wall of the Y-piece in the areas of the separate flow paths that extend in parallel to one another.

An especially great certainty of measurement is obtained if the holes in the outer wall lead into at least one buffer volume, whose inner pressure can be measured. The number of holes may be selected to be relatively large because the individual holes do not need to be provided with pressure pipes. As a result, there will be a high tolerance to the clogging of individual holes, and slight variations or inhomogeneities in the flow will also have only a reduced effect on pressure measurement. Such a buffer volume is advantageously associated with each pressure measuring means.

In another advantageous embodiment of a device according to the present invention, openings, which can be connected with pressure measuring means via channels extending in the interior of the partition, are arranged in the partition in the areas of the separate flow paths that extend in parallel to one another. The number of flexible tubes leading into the vicinity of the patient is reduced as a result.

It is especially advantageous if two means of the same type for obtaining measured values to characterize the flowing gas are coupled in the separate flow paths such that they make possible a difference measurement between the separate flow paths. It is usually possible due to the difference measurement to determine the flow component of changing direction in case a continuous basic flow is superimposed to a flow of changing direction. Dead space rinsing by a basic flow is necessary in some medical applications. The field of use of the device according to the present invention is thus expanded by the difference measurement.

An especially advantageous embodiment with the possibility of measuring the pressure difference between the separate flow paths is obtained if a movable part is integrated in the partition and it is provided with measuring means, and the movable part sends a signal that depends on the pressure difference by its deflection in case of a pressure difference between the separate flow paths. This can be embodied, for example, by a piezo measuring element.

An alternative embodiment with the possibility of measuring the pressure difference between the separate flow paths is obtained if windows that are permeable to ultrasound and are located approximately on a straight line that is sloped against the direction of flow are arranged in the partition and in the outer walls of the Y-piece in the area in which the separate flow paths extend in parallel to one another, and ultrasound transducers, which form a measuring section between them, via which flow measurement can be carried out by time of flight measurement, are arranged in front of the windows outside the flow paths.

A further improvement of the accuracy of measurement and reproducibility is achieved if flow rectifiers are arranged in the direction of flow in front of the particular site at which measured values are obtained to characterize the flowing gas. These may be various flow guide vanes which ensure a sufficiently stable laminar flow at the particular measuring site in case of complicated incoming flow conditions.

Devices according to the present invention will be described in greater detail below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is a schematic sectional view of a device according to the present invention in the area of the Y-piece with chip sensors integrated in the outer wall;

FIG. 10 is a schematic sectional view of a portion of a device according to the present invention with a movable flap at the end of the partition in the connection area to the tube adapter;

FIG. 10.1 is an enlarged schematic sectional view of the device of FIG. 10 showing the movable flap at the end of the partition in the connection area to the tube adapter;

FIG. 11 is a schematic sectional view of the portion of the device according to FIG. 10 showing a different position of the movable flap at the end of the partition in the connection area to the tube adapter;

FIG. 11.1 is an enlarged schematic sectional view of the device of FIG. 10 showing the movable flap at the end of the partition in the connection area to the tube adapter; and FIG. 12 is a schematic sectional view of a device according to the present invention in the area of the Y-piece with buffer volume and flow guide vanes.

DESCRIPTION OF THE PREFERRED EMBODIMENTS

Figure 1:
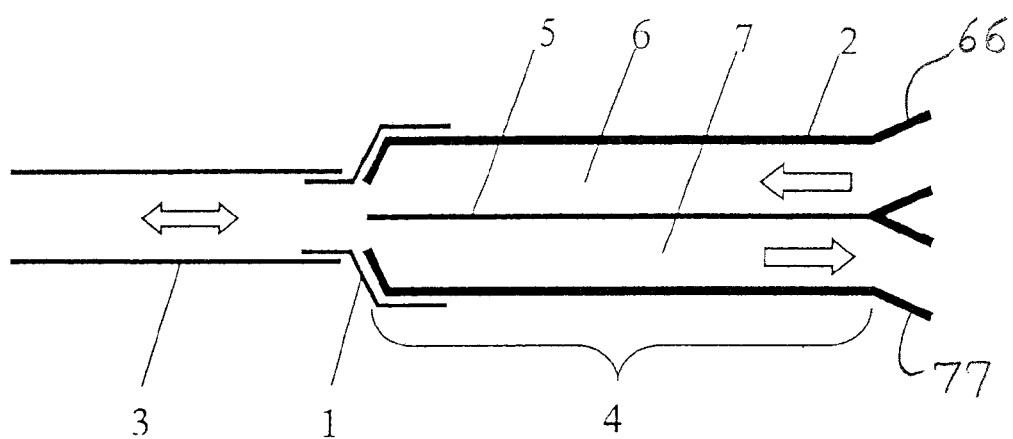
FIG. 1 is a schematic sectional view of a device according to the present invention in the area of the Y-piece.

Referring to the drawings in particular, FIG. 1 shows a Y-piece 2 according to the present invention connected to a tube 3 via a tube adapter 1 in a respiration unit for mechanical respiration. The base area (or parallel section) 4 of the Y-piece is divided by a flat partition 5 into two separate flow paths 6, 7 extending in parallel to one another. During respiration, inspiration takes place via one flow path 6, and expiration via the other flow path 7. Both flow paths extend at first direction flow passage 66 and second direction flow passage 77 to the connection pieces (not shown here) of the Y-piece 2, to which additional gas-carrying components, such as breathing tubes or the like, may be connected. On the patient side, the separation of the flow paths 6, 7 ends in the area of the tube adapter 1 (ends at an opening that is a bidirectional flow passage or the bidirectional flow opening with the tube adapter forms a bidirectional flow passage). The base area 4 of the Y-piece 2 does not contribute to the dead volume of the respiration unit. The uncoupling of the separate flow paths is improved compared with respiration units with conventional Y-pieces. A flow, whose direction can reverse, prevails in the tube 3 only. The arrows shown illustrate possible directions of flow in the respective sections of the device according to the present invention. Flow conditions that permit reliable measurement of different parameters of the flowing gases prevail in the flow paths 6, 7 extending in parallel to one another in the base area 4 of the Y-piece 2, as a result of which a measuring site located very close to the patient is explored, at which flows without reversal of direction can be measured. The measuring technique is simplified as a result.

Figures 2A, 2B:
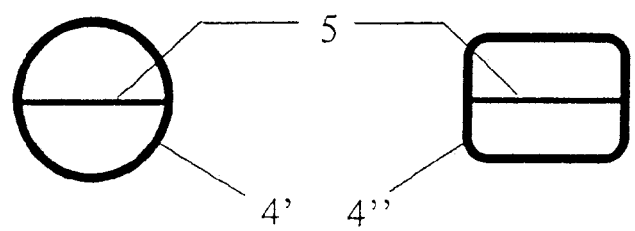
FIG. 2A is a cross sectional view of a Y-piece according to the present invention in the area in which the separate flow paths extend in parallel to one another.
FIG. 2B is a cross sectional view of another Y-piece according to the present invention in the area in which the separate flow paths extend in parallel to one another.

In special embodiments of the base area 4 of the Y-piece 2, the base area has, according to FIG. 2A a round cross section 4' or according to FIG. 2B an approximately square cross section 4''. It is divided by a flat partition 5, 5 in both cases. The embodiment with approximately square cross section (FIG. 2B) can, in particular, be advantageously combined with planar sensors (not shown).

Figure 3:
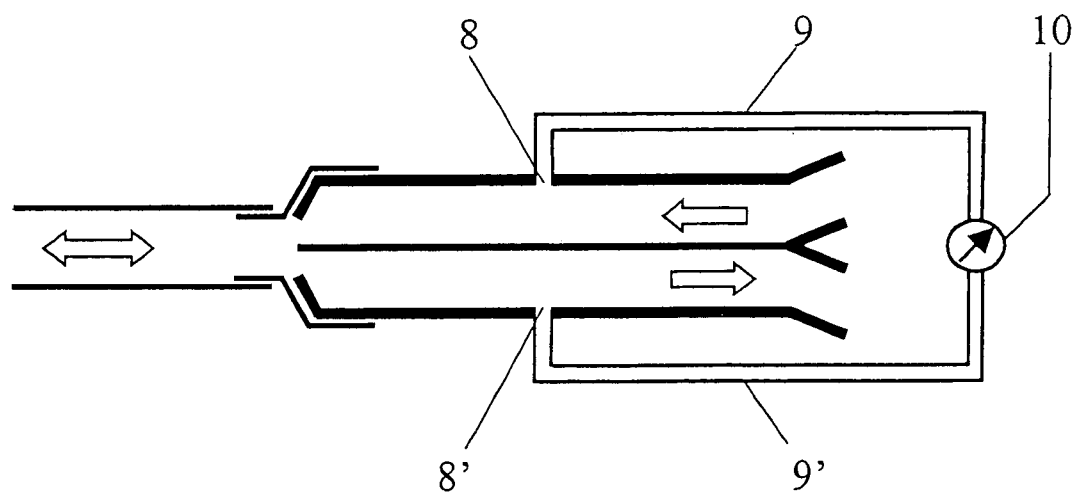
FIG. 3 is a schematic sectional view of a device according to the present invention in the area of the Y-piece with holes for pressure measurement in the area of the outer wall.

FIG. 3 shows a variant of a device according to the present invention, in which the static pressure in the flow paths 6, 7 can be measured via holes 8, 8'. A pressure measuring device 10 is connected via flexible tubes 9, 9'. Measurements of the differential pressure can also be carried out with this configuration.

Figure 4:
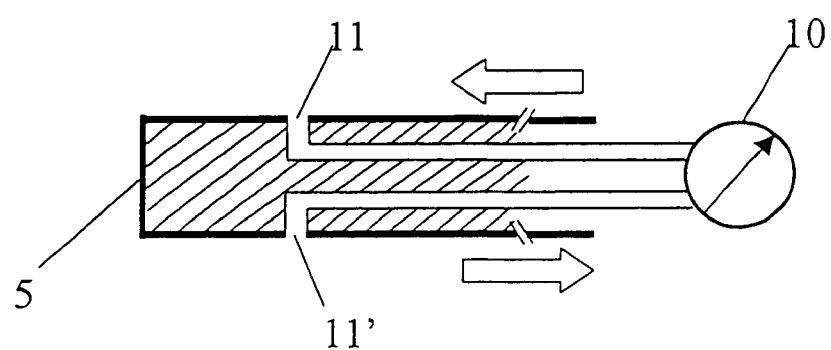
FIG. 4 is a schematic sectional view of a partition according to the present invention with channels milled in for pressure measurement.

FIG. 4 shows a modified form of a flat partition 5 according to the present invention, in which channels 11, 11' are milled, which are connected with a pressure measuring device 10. Measurement of the static pressure can also be measured with this arrangement in the areas of the separate flow paths that extend in parallel to one another. One advantage of this design is the reduced number of flexible tubes leading into the patient's immediate vicinity and the possibility of a highly compact design.

Figure 5:
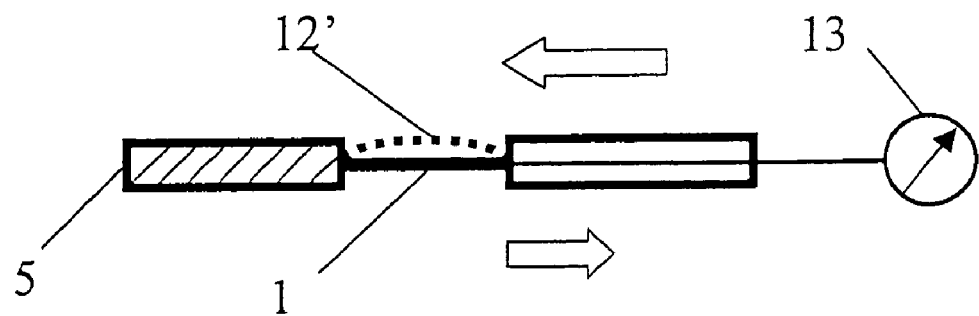
FIG. 5 is a schematic sectional view of a partition according to the present invention with integrated piezo pressure measuring element.

FIG. 5 shows a modified form of a flat partition 5 according to the present invention, in which a piezo pressure measuring element 12 is integrated. When a differential pressure is present, the resulting action of the force produces a deflection from the inoperative position of the piezo pressure measuring element 12 into another position 12'. As a result, an evaluable voltage is generated, which can be processed with a voltage measuring device 13 or corresponding evaluating units (not shown).

Figure 6:
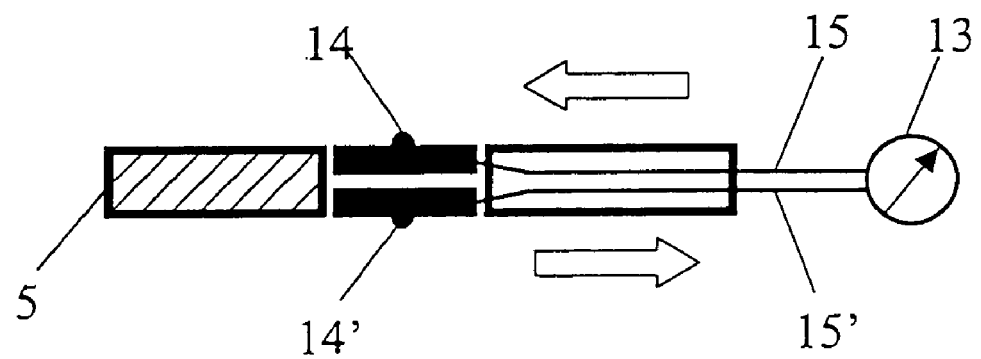
FIG. 6 is a schematic sectional view of a partition according to the present invention with integrated chip sensors.

FIG. 6 shows a modified form of a flat partition 5 according to the present invention, in which planar measuring elements 14, 14' are integrated for flow measurement. Each of these measuring elements sends a signal via electric lines 15, 15' integrated in the partition, and this signal can be processed with a voltage measuring device 13 or corresponding evaluating units (not shown). This embodiment is likewise characterized by a highly compact design and can be used to measure individual flows as well as flow differences.

Figure 7:
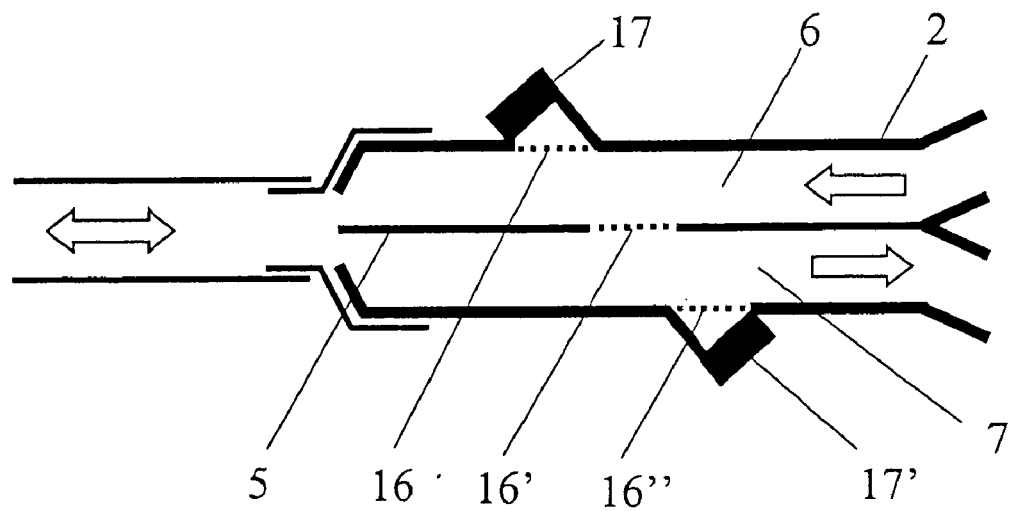
FIG. 7 is a schematic sectional view of a device according to the present invention in the area of the Y-piece with integrated ultrasound measuring path.

FIG. 7 shows a variant of a device according to the present invention, in which windows 16, 16', 16'', which are permeable to ultrasound and are located on a straight line that is sloped against the direction of flow, are arranged in the partition 5 and the outer walls of the Y-piece 2 in the area in which the separate flow paths 6, 7 extend in parallel to one another. Ultrasound transducers 17, 17', which form a measuring section between them, via which flow measurement can be carried out by time of flight measurement, are arranged in front of the outer windows 16, 16' outside the flow paths 6, 7. The advantage of this arrangement is that no sensor needs to be directly exposed to a flow to be measured and no sensor can thus distort the flow due to geometric effects.

Figure 8:
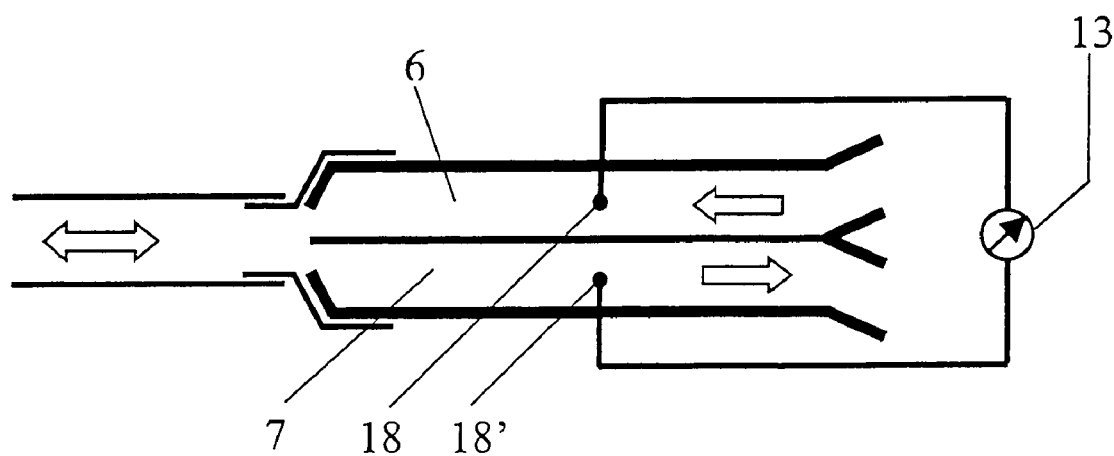
FIG. 8 is a schematic sectional view of a device according to the present invention in the area of the Y-piece with integrated hot wire sensors for flow measurement.

FIGS. 8 and 9 show a schematic sectional view of a device according to the present invention in the area of the Y-piece with integrated hot wire sensors 18, 18' directly in the flow to be measured or with planar chip sensors 19, 19' for flow measurement at the outer walls of the Y-piece 2 that limit the flow paths 6, 7. The measured signals are sent in both cases to a voltage measuring device or a corresponding evaluating unit. Individual or difference measurements are possible.

FIGS. 10, 10.1 and 11, 11.1 show schematic views of a device according to the present invention with a movable flap 20 at the end of the flat partition 5 in the connection area to the tube adapter 1 during inspiration (FIG. 10) and during expiration (FIG. 11) as well as corresponding enlarged views (FIGS. 10.1, 11.1) of the area of the connection between the movable flap 20 and the flat partition 5. During inspiration, the movable flap 20 is in a position in which it reduces the flow cross section of the flow path 6, through which the inspiration takes place, only slightly. If the direction of flow changes, the gas flow arriving at the movable flap 20 stands up the movable flap 20 until the latter assumes a position determined by a fixed stop, in which it markedly reduces the flow cross section of the flow path 6 for the inspiration. At the same time, it acts as a guide vane for the flow path 7 for the expiration and thus facilitates the inflow of the expiration flow into the flow path 7. An especially effective uncoupling of the separate flow paths 6, 7 is achieved as a result. FIGS. 10.1 and 11.1 show a design principle that makes possible a flap movement just described. The front side of the flat partition 5 has the shape of a flat notch. The flanks 22, 23 of this notch are at an obtuse angle with one another. In areas in which the flanks 22, 23 touch each other, the movable flap 20 is fastened to the flat partition 5 with elastic fastening means 21. The position of the flanks 22, 23 determines the position of two stop positions. The elastic fastening means 21 are pretensioned such that without gas flow or during inspiration, the movable flap 20 is in contact with the flank 23 in one stop position and can be moved into the other stop position, in which there is contact with the flank 22, due to incoming flow during expiration.

FIG. 12 shows a variant of a device according to the present invention, in which holes 8, 8' in the outer wall of the Y-piece lead into buffer volumes 24, 24', whose internal pressure is monitored. If an individual hole is closed due to clogging, this has hardly any effect on the pressure measurement, because each of the buffer volumes 24, 24' communicates with the gas flow to be measured via a plurality of holes 8, 8'. Flow rectifiers in the form of guide vanes 25, 25', which ensure an especially uniform flow behavior, which in turn leads to especially reliable and reproducible measured values, are arranged in front of the site of pressure measurement in the direction of flow, i.e., in this case in front of the holes 8, 8', which also corresponds at the same time to the site at which measured values for characterizing the flowing gas are obtained according to claim 16.

While specific embodiments of the invention have been shown and described in detail to illustrate the application of the principles of the invention, it will be understood that the invention may be embodied otherwise without departing from such principles.

What is claimed is:

1. A device for measuring the volume flow of a gas, whose direction of flow can reverse, the device comprising:
   an arrangement with a Y-piece with one end of said arrangement connected to a component through which gas flows and in which changing directions of flow may prevail, and with other ends connected with components through which gas flows and in which there is no change in the direction of flow, said Y-piece having separate uncoupled flow paths for gas flows with different directions of flow, which extend in parallel and are separated from one another by a flat partition in the area in which said uncoupled flow paths for gas flows with different directions of flow extend in parallel to one another, with said partition extending to a partition end defining a transition from said gas flows in which changing directions of flow may prevail to said different directions of flow extending in parallel to one another, said arrangement being equipped with means for obtaining measured values to characterize the flowing gas in an area in which different directions of flow extend in parallel to one another.

2. A device in accordance with claim 1, further comprising a movable flap that moves between two positions, said movable flap being fastened to said partition end, wherein said flap assumes a position that reduces a flow cross section as little as possible in case of a direction of flow from the Y-piece to said component through which gas flows and in which changing directions of flow can prevail, and in case of a reversed direction of flow it assumes a position in which it facilitates an inflow into a flow path intended for that direction of flow.

3. A device in accordance with claim 2, further comprising an end stop functionally cooperating with said movable flap wherein at least one of the two positions of said movable flap is determined by said end stop.

4. A device in accordance with claim 2, wherein said movable flap is fastened such that the position of the movable flap is set by flow forces acting on said movable flap.

5. A device in accordance with claim 2, further comprising an elastic fastening means between said movable flap and a flat partition wherein the mobility of said flap is achieved by said elastic fastening means.

6. A device in accordance with claim 1, wherein a cross section of said Y-piece is approximately round or approximately square in the area in which the separate flow paths extend in parallel to one another.

7. A device in accordance with claim 1, wherein said means for obtaining measured values to characterize the flowing gas comprises hot wire sensors arranged for flow measurement in the areas of the separate flow paths that extend in parallel to one another.

8. A device in accordance with claim 1, wherein said means for obtaining measured values to characterize the flowing gas comprises chip sensors arranged for flow measurement in or at an outer wall of the Y-piece or in or at the flat partition in the areas of the separate flow paths that extend in parallel to one another.

9. A device in accordance with claim 1, further comprising openings, through which pressure measurement can be carried out when the openings are connected with said means for obtaining measured values via pressure lines, said openings being arranged in an outer wall of the Y-piece in the areas of the separate flow paths that extend in parallel to one another.

10. A device in accordance with claim 9, further comprising buffer volumes, wherein said openings each lead into one of said buffer volumes and said buffer volumes have an internal pressure that can be measured.

11. A device in accordance with claim 1, further comprising openings, through which pressure measurement can be carried out with said openings connected with said means for obtaining measured values via channels extending in the interior of the partition, said openings being arranged in the flat partition in areas of the separate flow paths that extend in parallel to one another.

12. A device in accordance with claim 1, wherein said means for obtaining measured values comprises a first flow measuring device operatively connected to one of said uncoupled flow paths and a second flow measuring device operatively connected to another of said uncoupled flow paths such that to provide a difference measurement between said one and said another flow paths.

13. A device in accordance with claim 1, wherein a movable part is integrated in the flat partition and is provided with said means for obtaining measured values, said movable part sending a signal that depends on a pressure difference due to a deflection of said movable part in case of a pressure difference between the separate flow paths.

14. A device in accordance with claim 1, wherein
said means for obtaining measured values includes windows permeable to ultrasound are arranged in the flat partition and outer walls of the Y-piece in the area in which the separate flow paths extend in parallel to one another;
the windows are located on a straight line that is sloped against the direction of flow;
said means for obtaining measured values to characterize the flowing gas comprise ultrasound transducers forming a measuring section between them and arranged in a front of the windows outside the flow paths; and
a flow measurement can be performed via said measuring section by time of flight measurement.

15. A device in accordance with claim 1, further comprising flow rectifiers arranged in a direction of flow upstream of said means for obtaining measured values to characterize the flowing gas.

16. A device for measuring properties of a gas, the device comprising:
a bidirectional flow passage through which gas flows alternates between flow in a first direction and flow in a second direction;
a first direction flow passage connected to said bidirectional flow passage, said first direction flow passage having gas flow in said first direction;
a second direction flow passage connected to said bidirectional flow passage, said second direction flow passage having gas flow in said second direction;
a parallel section connected to said with bidirectional flow passage, said first direction flow passage and said second direction flow passage and defining essentially uncoupled flow paths for gas flows with different directions of flow, which extend in parallel at least partially, said uncoupled flow paths being separated from one another by a flat partition in an area in which said uncoupled flow paths for gas flows with different directions of flow extend in parallel to one another and said flat partition having an end adjacent to said bidirectional flow passage and cooperating with said bidirectional flow passage to define a transition region between bidirectional flow in said bidirectional flow passage and uncoupled flow paths separated by said flat partition;
measurement means for obtaining volume flow measured values to characterize the flowing gas in the area in which said uncoupled flow paths for gas flows with different directions of flow extend in parallel to one another.

17. A device in accordance with claim 16, wherein said flat partition extends into or adjacent to said bidirectional flow passage to define said transition region.

18. A device in accordance with claim 16, further comprising:
a movable flap that moves between two positions, said movable flap being fastened to said end of said flat partition, wherein said flap assumes a position that reduces the flow cross section as little as possible in case of a direction of flow from the device to said bidirectional flow passage and in case of the reversed direction of flow assumes a position in which it facilitates an inflow into one of said first direction flow passage or second direction flow passage; and
an end stop functionally cooperating with said movable flap wherein at least one of the two positions of said movable flap is determined by said end stop.

19. A device in accordance with claim 16, wherein said means for obtaining measured values comprises one or more of:
hot wire sensors arranged for flow measurement in the areas of the separate flow paths that extend in parallel to one another;
sensors arranged for flow measurement in or at an outer wall of the device or in or at the flat partition;
a movable part integrated in the flat partition and provided with measuring means sending a signal that depends on a pressure difference due to its deflection in case of a pressure difference between the separate flow paths;
a combination including windows permeable to ultrasound arranged in the flat partition and outer walls of the Y-piece in the area in which the separate flow paths extend in parallel to one another, the windows being located on a straight line that is sloped against the direction of flow and ultrasound transducers forming a measuring section between them and arranged in a front of the windows outside the flow paths.

20. A device for measuring the volume flow of a gas, whose direction of flow can reverse, the device comprising:
an arrangement with a Y-piece with one end connected to a component through which gas flows and in which changing directions of flow may prevail, and whose other ends are connected with components through which gas flows and in which there is no change in the direction of flow, said Y-piece having separate, essentially uncoupled flow paths for gas flows with different directions of flow, which extend in parallel at least partially, are separated from one another by a flat partition in the area in which said uncoupled flow paths for gas flows with different directions of flow extend in parallel to one another, and are equipped with means for obtaining measured values to characterize the flowing gas in the area in which they extend in parallel to one another; and
a movable flap fastened to an end of said flat partition in a region in which changing directions of flow may prevail and in or adjacent to said component through which gas flows and in which changing directions of flow may prevail, said flap moving between two positions, wherein said flap assumes a position that reduces a flow cross section as little as possible in case of a direction of flow from the Y-piece to the gas-carrying component, and in case of the reversed direction of flow said movable flap assumes a position in which said movable flap facilitates the inflow into the flow path intended for that direction of flow.

* * * * *